United States Patent [19]

Salzman et al.

[11] Patent Number: 4,857,471
[45] Date of Patent: Aug. 15, 1989

[54] ANALYZER WITH WASH STATION SEPARATE FROM INCUBATOR

[75] Inventors: Catherine A. Salzman; Martin F. Muszak, both of Rochester, N.Y.

[73] Assignee: Eastman Kodak Company, Rochester, N.Y.

[21] Appl. No.: 75,476

[22] Filed: Jul. 20, 1987

[51] Int. Cl.[4] .................................. G01N 35/00
[52] U.S. Cl. ........................ 436/43; 436/48; 422/65; 422/99
[58] Field of Search ............ 436/43, 46, 47, 48; 422/65, 66, 52, 99

[56] References Cited

U.S. PATENT DOCUMENTS

| | | |
|---|---|---|
| 4,113,436 | 9/1978 | Werder et al. .................. 422/65 |
| 4,265,855 | 5/1981 | Mandle et al. .................. 422/65 |
| 4,296,069 | 10/1981 | Smith et al. . |
| 4,303,611 | 12/1981 | Jessop .................. 422/65 |
| 4,512,952 | 4/1985 | Blanding et al. . |
| 4,517,288 | 5/1985 | Giegel et al. . |
| 4,539,855 | 9/1985 | Jacobs . |
| 4,568,519 | 2/1986 | Hamilton et al. . |
| 4,584,275 | 4/1986 | Okano et al. .................. 422/65 |
| 4,675,162 | 6/1987 | Sakamaki et al. .................. 422/65 |

Primary Examiner—Michael S. Marcus
Assistant Examiner—D. John Griffith, Jr.
Attorney, Agent, or Firm—Dana M. Schmidt

[57] ABSTRACT

There are described the apparatus and a process for using it, wherein a wash station is provided apart from a continuously rotating incubator. Means are provided for moving a test element to the wash station before or in the middle of its incubation, and from the wash station to the incubator after it is washed.

12 Claims, 5 Drawing Sheets

ANALYZER WITH WASH STATION SEPARATE FROM INCUBATOR

FIELD OF THE INVENTION

The invention relates to an analyzer for ascertaining analyte concentrations in body liquids dispensed onto test elements, particularly such analyzers that need a wash station to allow immunoassays to be conducted.

BACKGROUND OF THE INVENTION

Analyzers are known which automatically process a test element, sometimes labeled a "slide", that has all of the necessary reagents in a dried format, so as to generate a signal indicative of the concentration of an analyte of a body liquid. Such analyzers include a station for supplying test elements, a station for dispensing an aliquot of body liquid, such as serum, onto a test element, a station for incubating a test element containing that aliquot, a station for detecting the signal produced by the test element, and means for moving such test element between such stations. Examples of such analyzers are shown in U.S. Pat. Nos. 4,539,855 and 4,568,519 issued on Sept. 10, 1985 and Feb. 4, 1986, respectively.

In such analyzers, particularly in the portion doing rate analysis wherein the rate of change in signal generated by the test element is measured, the incubating station keeps the test element(s) for the entire incubation, so that each such element is not removed therefrom until all readings are completed. That is, after the final reading, preferably a photometric reading, is taken, a test element in such an incubator is picked out of the incubator and dropped into a disposal bin. A useful construction of an incubator and picker capable of this function is shown in FIGS. 2 and 2a of the aforesaid U.S. Pat. No. 4,568,519.

Such a construction does not make it possible to easily wash the test element with, e.g., water, after partial incubation and prior to a first reading at the read station. (Such a wash step is useful in certain assays, such as immunoassays, to separate reaction product, e.g., complexed antibody and antigen, from unreacted reagent, e.g., antibody or antigen not yet complexed.) That is, the logical step would be to add wash liquid to the test element through the top of the incubator, while the test element remains in the incubator. Such analyzers are in fact known in the industry. However, the incubator is constantly rotating the test elements, even while making photometer readings, in order to make 10 or so readings per minute as is needed for accurate rate analysis. The only stoppage occurs for two seconds for loading and unloading test elements. It is not feasible to try to wash test elements "on the fly" in such an incubator.

Thus, prior to this invention there has been an unsolved need to provide a wash station in an automated analyzer for allowing the washing of a test element to force separation of reaction product and unreacted reagent. This need particularly has not been met for use with an incubator in which the test elements are constantly rotating therein except when being loaded and unloaded.

SUMMARY OF THE INVENTION

We have devised an analyzer construction in which means are provided for washing a test element outside of the incubator, during the incubation cycle of the incubator.

More specifically, in accord with one aspect of the invention, there is provided an analyzer for processing a test element to determine analytes of a body liquid, the analyzer comprising means for moving a test element bearing a body liquid, through the analyzer; means for incubating such a test element, and means for detecting a signal generated in the test element after incubation, indicative of the concentration of the analyte. The analyzer is improved in that it further includes a wash station adjacent to the incubator for washing a test element with liquid, and second means for moving a test element to the wash station, and from the wash station to the incubating means; whereby a wash step capable of separating reaction product from reagents, is available in the analyzer.

In accord with a second aspect of the invention, there is provided such an analyzer, improved in that it further includes a wash station adjacent to said incubator for washing a test element with liquid, and second means for moving a test element (a) out of the incubating means, (b) to the wash station, and (c) from the wash station back to the incubating means, whereby a wash step capable of separating reaction product from reagents, is available in the analyzer.

In accord with a third aspect of the invention, there is provided a method of analyzing a body liquid for the concentration of an analyte present, such method comprising the steps of incubating at an incubation station, a test element on which a body liquid has been dispensed, such test element comprising the necessary reagents to produce a detectable signal in response to the presence of a particular analyte; and thereafter detecting such detectable signal and converting it into a measure of concentration of the analyte. The method is improved in that the process includes the steps of:

(a) before or during the incubating step, moving such test element to a wash station apart from the incubating station;

(b) after step (a), dispensing a wash liquid at the wash station onto the moved test element; and thereafter (c) starting or finishing the incubating step at the incubation station.

Thus, it is an advantageous feature of the invention that a test element can be washed part-way through its incubation cycle, even when being incubated by incubating means that are continuously rotating.

It is a related advantageous feature of the invention that an analyzer using such incubating means can process immunoassays.

It is another advantageous feature of the invention that an analyzer is provided with test element wash capabilities that are outside of and removed from the incubator.

Other advantageous features will become apparent upon reference to the following Detailed Discussion, when read in light of the attached drawings.

DESCRIPTION OF THE PREFERRED EMBODIMENTS

The invention is described herein in the context of the preferred embodiments, wherein the analyzer features an incubator that is constantly rotating (except for loading and unloading), and a wash cycle that occurs in the middle of the incubation cycle. In addition, the invention is useful with an incubator of the start-stop variety, and also with an analyzer in which washing occurs before the test element is inserted into the incubator.

As used herein, terms such as "up, "down" and "vertical" refer to the orientation of parts as they are used in the analyzer.

Figure 1:
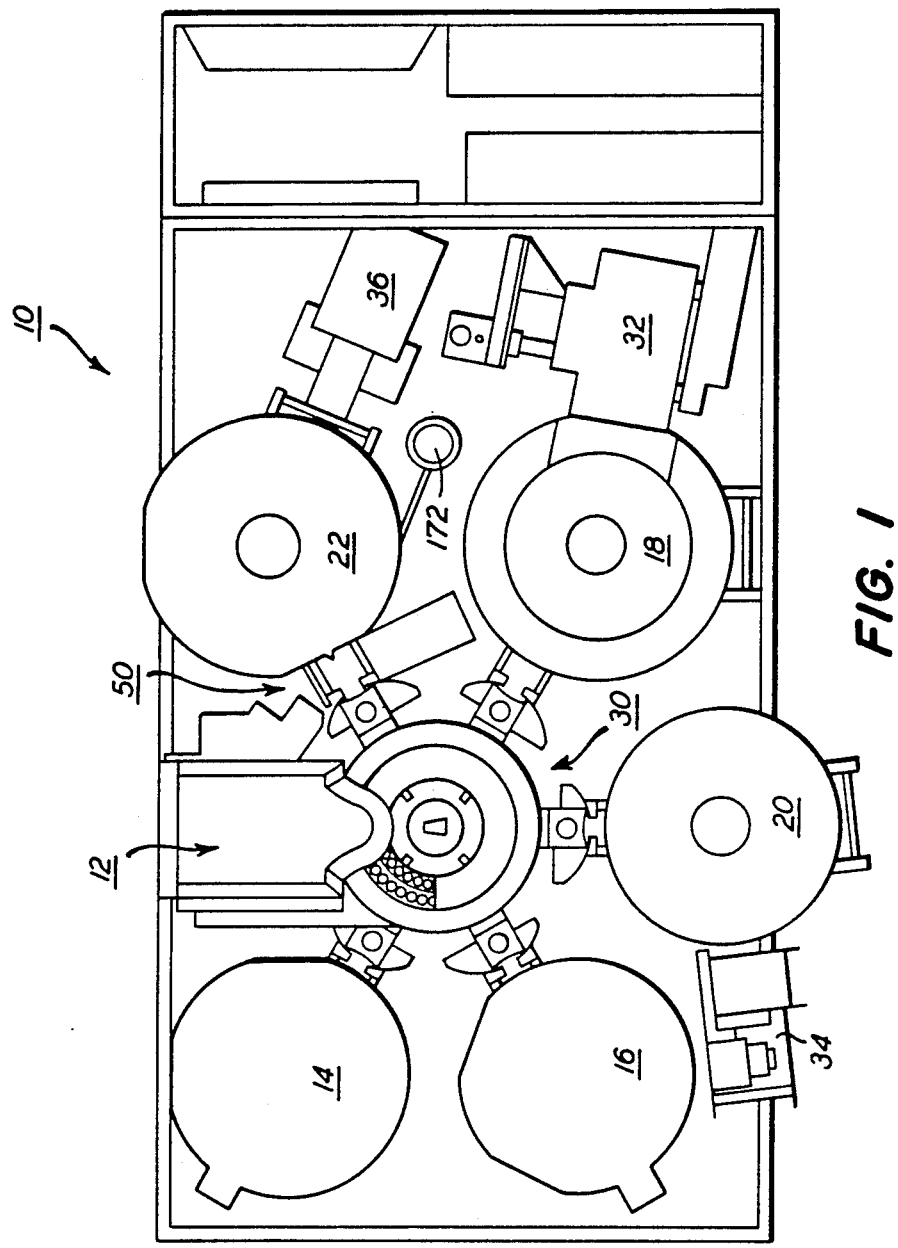
FIG. 1 is a plan view of an analyzer of the type to which the invention is particularly applicable.

An analyzer 10 with which the invention is particularly useful comprises, FIG. 1, a liquid dispensing station 12, two supply stations 14 and 16 for supplying colorimetric or potentiometric test elements, incubator stations 18, 20 and 22 for the different incubations required, element moving means for moving test elements between the stations, including a distributor mechanism 30 for moving test elements from the supply stations to the dispensing station 12 and the incubators, and appropriate read stations 32, 34 and 36 providing means for detecting a signal generated by the test element in question. Thus, incubator 18 is a colorimetric end-point incubator with a photometer at read station 32, incubator 20 is designed for potentiometric test elements read by potentiometer 34, and incubator 22 is a rate incubator with a constantly rotating rotor, except for loading and unloading, that cooperates with a photometer 36 that reads "on the fly". All of the aforementioned are conventional, so as to require no further details.

In accord with one aspect of the invention, wash station means 50 are provided adjacent incubator 22 to allow a test element to be washed prior to or during its incubation in incubator 22. Such means 50 comprises, FIG. 2, a picker assembly 60 for moving test elements into and out of incubator 22, a wash dispenser 130, and a train assembly 100 for shuttling a test element from picker assembly to the wash station and back.

With regard to the picker assembly 60, a test element is transferred from distributor 30, FIG. 1, to assembly 60 by shuttle fingers 64, operated conventionally by a motor (not shown). Picker assembly 60 includes picker fingers 66 each having a groove 68 formed in the undersurface 70 of the fingers, FIG. 2. Groove 68 is dimensioned to accommodate a test element E, with a pushing edge 72 and a pulling edge 74. Fingers 66 extend from a bracket 76 pivotally mounted at 77, FIGS. 2 and 3, on a block 78. Block 78 rides on a lead screw 80, FIG. 2, that is rotated by a pulley and belt 82 operated by motor 84.

Space is provided under the passageway of fingers 66, for the train assembly 100, discussed below.

On one side of that train assembly space is a diverter 90, raised and lowered by lever 92 and solenoid 94, so that used test elements can be diverted into a disposal bin 96. This diverter assembly is substantially identical in form and function to that shown in U.S. Pat. No. 4,568,519, the details of which are expressly incorporated herein by reference.

Train assembly 100 comprises preferably a pair of generally parallel guide surfaces, such as tracks 102, and a train of preferably three test element carriers 104, 106 and 108, each joined to an adjacent carrier at hinge pivots 110. Carrier 104 is connected to a drive lever 112 pivotally secured to an indexer disk 114 rotatably driven by motor 116. Each of carriers 104, 106 and 108 comprises a test element support surface 118 and holding flanges 120, 122 spaced from surface 118 a distance to accommodate a test element E therebetween. Carriers 104, 106 and 108 ride on tracks 102 by any suitable means, such as "Teflon"-filled plastic channels, or roller bearings (not shown).

Hinge pivots 110 are useful to allow the carriers to articulate downwardly after passing station 60. Alternatively, if the rest of the apparatus of analyzer 10 permits it, the carriers can be all one integral unit without pivots 110.

Figure 3A:
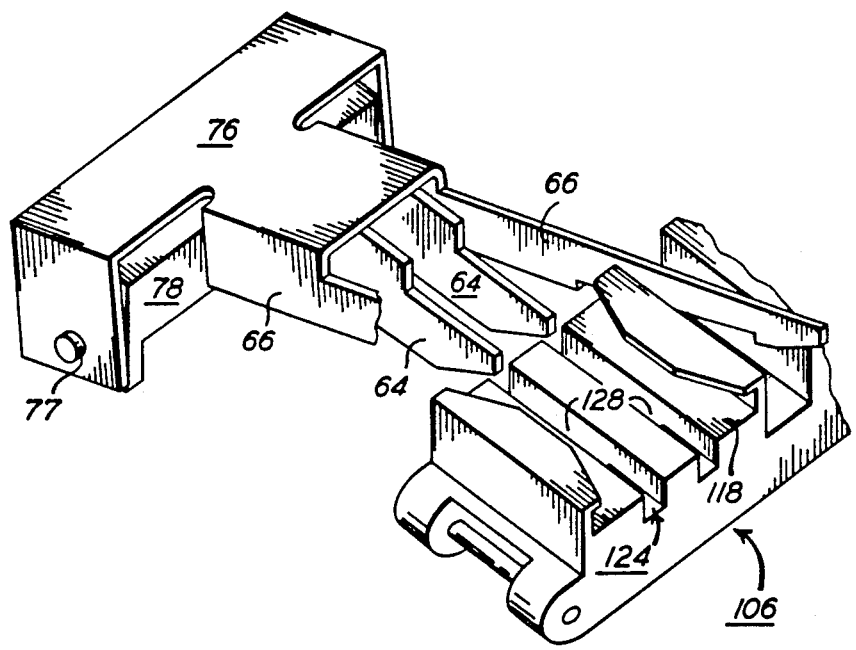
FIG. 3A is an isometric view of the cooperation between shuttle and picker fingers, with some parts broken away for clarity.
Figure 3B:
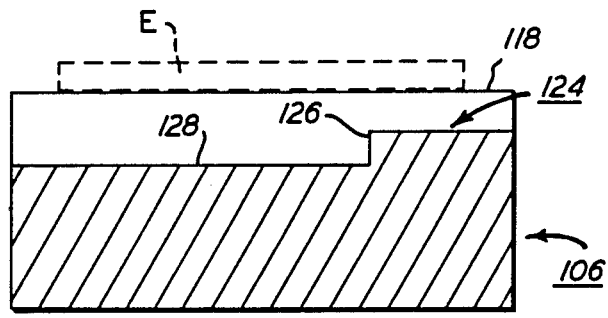
FIG. 3B is an elevational view in section of a test element carrier, taken through groove 124.

Support surface 118 of each carrier, Figs. 3A and 3B, is notched with a groove 124, that is stepped at 126 to provide a lower level 128. The lower level is used to accommodate shuttle fingers 64 when the shuttle inserts a test element E (shown in phantom) onto surface 118, FIG. 3A.

Figure 4:
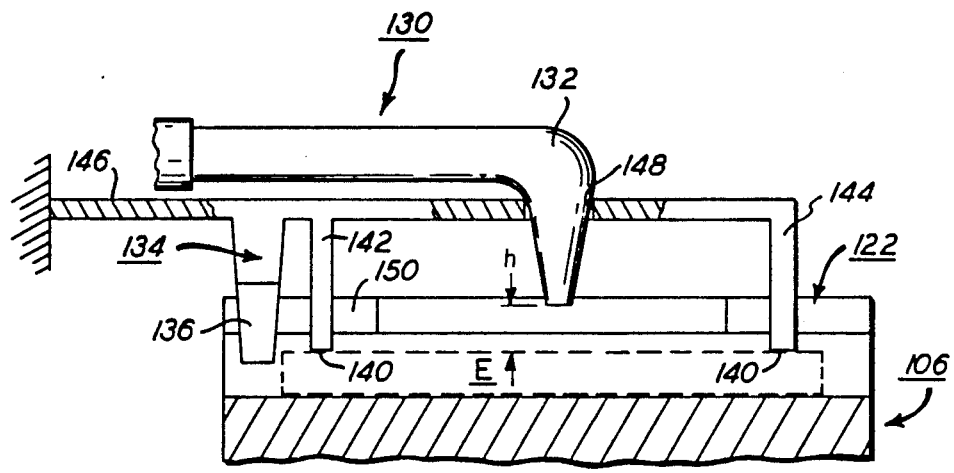
FIG. 4 is a fragmentary elevational view partly in section, through the wash dispenser of the invention.

Wash dispenser 130 comprises a dispensing nozzle 132, a cam 134 for raising and lowering nozzle 132 relative to test elements E, and reference surfaces 140, FIG. 4, used to accurately space nozzle 132 from the surface of elements E. Surfaces 140 are the bottom surfaces of fingers 142 and 144, extending from a flexible bracket 146 that mounts nozzle 132 in aperture 148. Bracket 146 also mounts cam 134 extending downwardly therefrom, surface 136 of cam 134 being dependent a further distance than is surface 140, to engage top surface 150 of flanges 120, 122 so as to raise nozzle 132 and fingers 142 out of the way of the flanges when the train of carriers 104, 106 and 108 is reciprocated. Reference surfaces 140 ride on the top surface of test element E as shown, to accurately space nozzle 132 the distance h from the test element that is optimum for the maximum rate of absorption of the wash liquid into the element. Most preferably, "h" is about 0.07 cm, which distance however will vary if the composition of test element E is significantly changed.

Figure 5:
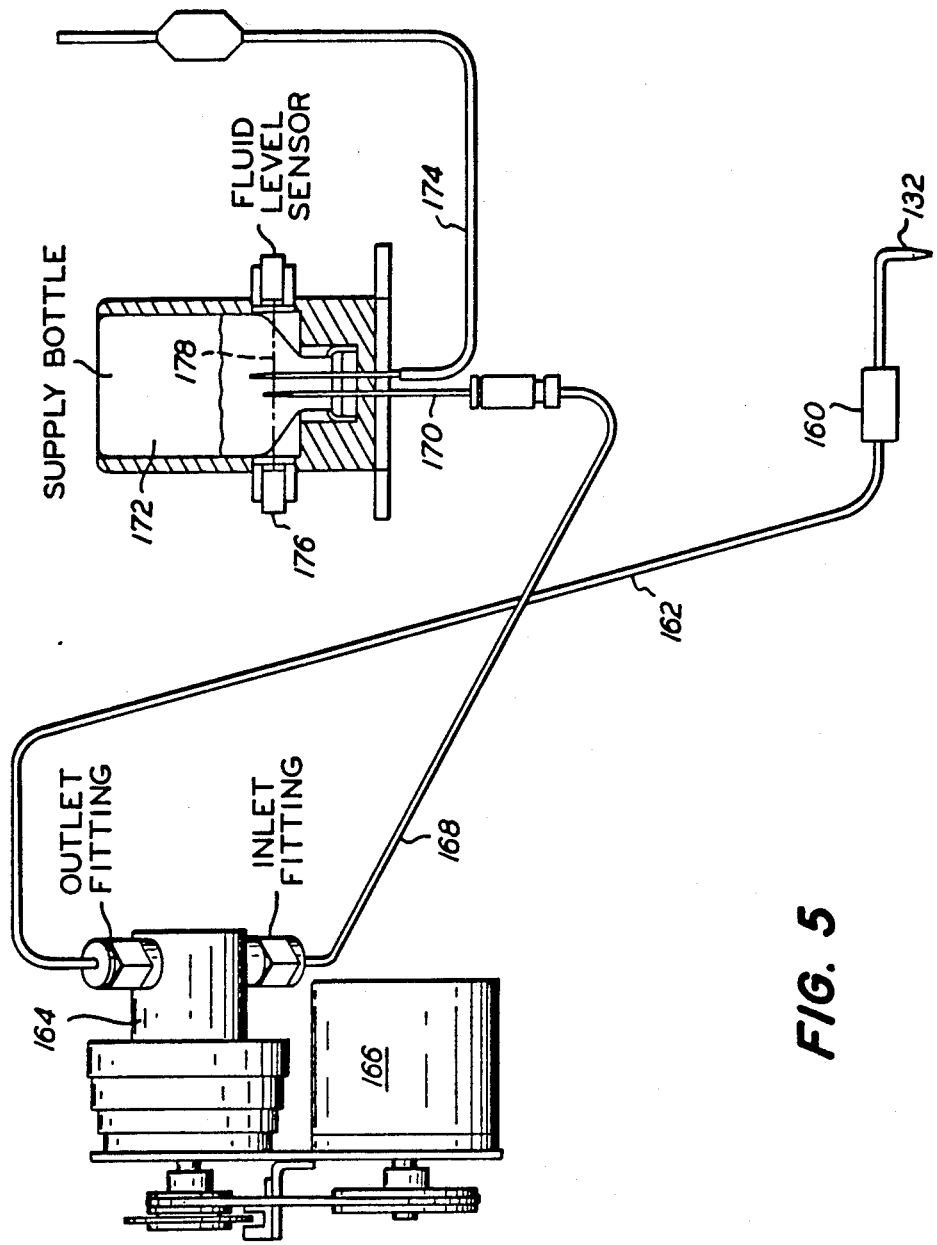
FIG. 5 is an elevational view, partly in section, of the plumbing for the wash dispenser.

To supply the wash liquid to nozzle 132, a fitting 160 is provided, that connects to an outlet line 162, FIG. 5. Line 162 is connected to a conventional pump 164 operated by a conventional motor 166. The wash liquid is brought into pump 164 by an inlet line 168, inserted via a needle 170 into supply bottle 172. A valving line 174 optionally vents bottle 172, and a conventional photoelectric sensor 176 is optionally included to emit an alarm when the wash liquid drops to a minimum level 178. The wash liquid can be either free of reagents, or it can contain one or more reagents such as a substrate for an enzyme label used in the immunoassay.

The operation of wash station 50 will be readily apparent from the preceding description. In brief, the preferred arrangement is to pull test elements out for washing only after part of the incubation has already occurred. However, it will be appreciated that the washing can be done prior to incubation by moving to the wash station a test element on train assembly 100 before it is pushed into incubator 22.

For the preferred operation, a test element is first inserted onto an empty carrier 104, 106 or 108 by shuttle fingers 64 extending under block 78 and into lower level 128 of grooves 124 of the carrier, FIG. 3A. For this operation, bracket 76 is pivoted by a lever, not shown, upwardly to the position shown in FIG. 3A, to move picker fingers 66 out of the way of shuttle fingers 64. Fingers 64 are then withdrawn and bracket 76 rotates back down to engage the test element so deposited. The incubator is then stopped, and fingers 66 are advanced towards the incubator to transfer the test element into the incubator. (All test elements are loaded into the incubator in this way.) After the first phase of the incubation is completed, incubator 22 is stopped briefly to allow a first test element to be picked out of the incubator by fingers 66 and pulled back to, preferably, carrier 104, FIG. 2. Carrier 104 is then moved in a direction (arrow 180) generally perpendicular to the motion (arrow 190) of test elements by picker fingers 66 until the first test element is under nozzle 132. At this time, a new test element is optionally loaded into the empty slot in the incubator. Cam 134 causes nozzle 132 to rise and fall o clear flanges 120, 122 (Arrow 200). While liquid is being dispensed, a second test element can be pulled out of incubator 22 (which again stops its continuous rotation just for this purpose) by the picker assembly. The second test element is dropped onto the train, e.g. onto carrier 106. (It will be readily apparent that that carrier may be a different one than the one the test element occupied when first supplied by shuttle fingers 64.) Train 100 is then reversed to move carrier 104 back under picker fingers 66, which push the first, now washed, test element back into incubator 22, again now stopped for this purpose. Alternatively, the washed test element can be retained in carrier 104 while the second test element is being washed at wash dispenser 130.

Finally, after each test element E is incubated and read while in incubator 22 (as is conventional), picker assembly 60 is activated once again, with diverter 90 raised, to pull the element out of stopped incubator 22 and down into bin 96.

Figure 2:
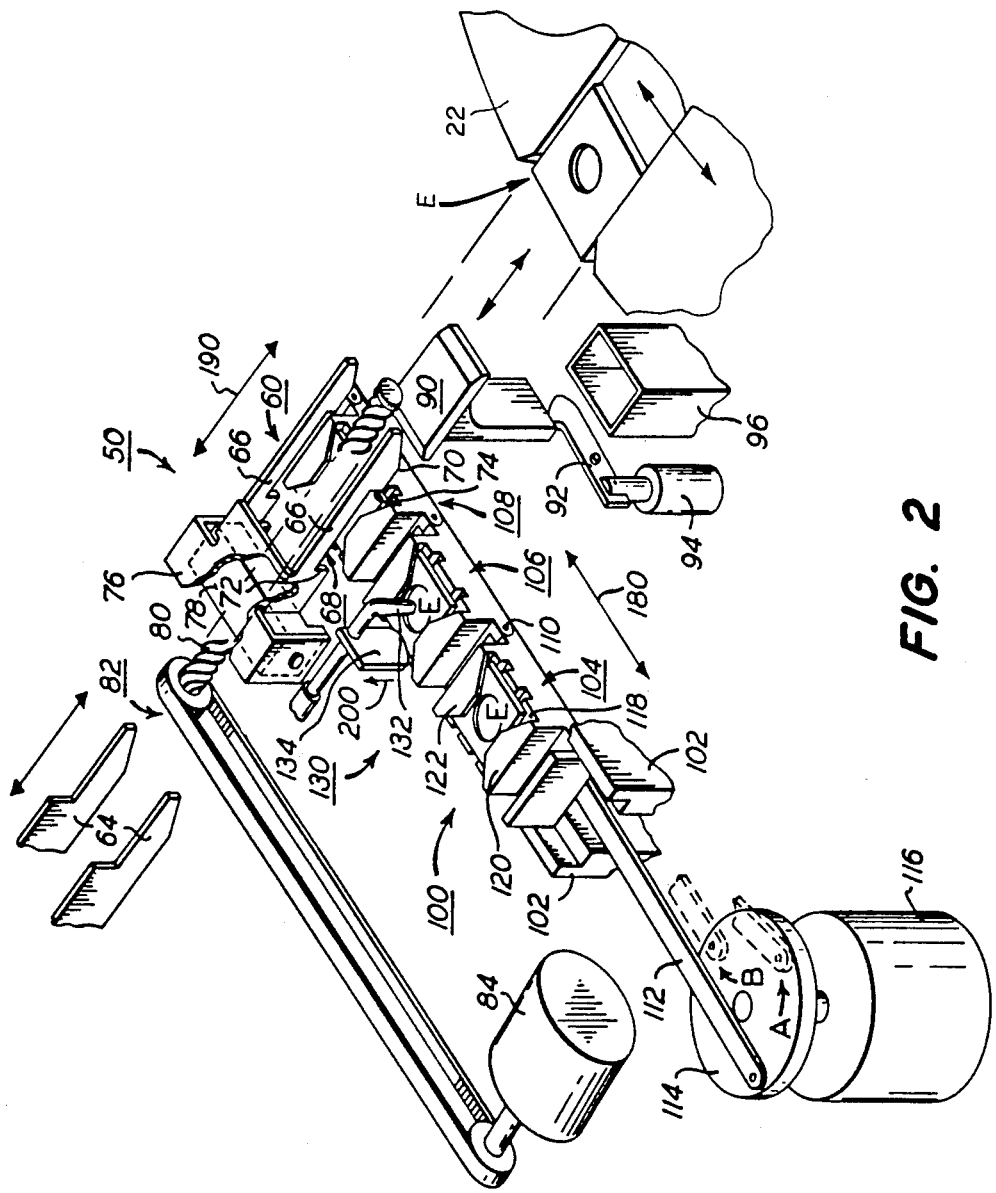
FIG. 2 is an isometric view, with parts broken away fro clarity, of the wash station provided by the invention.

The alternative positions of lever 112 to move carrier 106, and then carrier 104, into position under picker fingers 66, are shown in phantom, FIG. 2, positions A and B.

By the aforedescribed means, it will be apparent that washing is achieved without interfering with the otherwise continuous rotation of incubator 22. By doing the washing "off-line", the time it takes for the actual application of wash liquid (about 20 sec.) is time that is not wasted in keeping incubator 22 stopped, since the stop and start operation for removing a slide with picker fingers 66 only takes about 2 sec.

The invention has been described in detail with particular reference to preferred embodiments thereof, but it will be understood that variations and modifications can be effected within the spirit and scope of the invention.

What is claimed is:

1. In an analyzer for processing a slide element to determine analytes of a body liquid, the analyzer comprising
means for moving a plurality of slide elements bearing a body liquid, each independently through the analyzer;
means for incubating each slide element;
and means for detecting a signal generated in the slide element after incubation, indicative of the concentration of the analyte;
the improvement wherein said analyzer further includes a wash station off-line from said incubator and adjacent to said incubator, for washing a slide element with liquid, and second means capable of moving a slide element independently of others in said incubator, to said wash station, and from said wash station to said incubating means;
whereby a wash step capable of separating reaction product from reagents, is available for independent ones of said elements in the analyzer.

2. In an analyzer for processing a slide element to determine analytes of a body liquid, the analyzer comprising
means for moving a plurality of slide elements bearing a body liquid, each independently through the analyzer;
means for incubating each element;
and means for detecting a signal generated in the slide element after incubation, indicative of the concentration of the analyte;
the improvement wherein said analyzer further includes a wash station off-line from said incubator and adjacent to said incubator for washing a slide element with liquid, and second means capable of moving a slide element independently of other slide elements in said incubator, (a) out of said incubating means, (b) to said wash station, and (c) from said wash station back to said incubating means,
whereby a wash step capable of separating reaction product from reagents, in available for independent ones of said slide elements in the analyzer.

3. An analyzer as defined in claims 1 or 2, wherein said second means for moving a slide element includes means for conveying an incubated slide element to and from said wash station, and picker means for pushing and pulling a slide element into and out of, respectively, said incubator and onto said conveying means.

4. An analyzer as defined in claim 3, wherein said picker includes drive means for moving it from a first position wherein it receives a slide element, to a second position to place or remove said slide element in or from said incubator, to said first position or a third position on said conveying means, and to a fourth position at which said slide element is discarded.

5. An analyzer as defined in claim 3, wherein said conveying means includes at least two carriers for slide elements joined together and means for driving said at least two carriers into and out of position relative to said picker.

6. An analyzer as defined in claim 5, wherein said carriers are mounted for reciprocation along a guide surface that extends generally perpendicularly to the direction said picker pushes and pulls said slide elements.

7. An analyzer as defined in claim 3, and further including means for dispensing wash liquid at said wash station onto a slide element on said conveying means, and means for properly spacing said wash station above conveyed slide elements.

8. An analyzer as defined in claim 7, wherein said spacing means include means for reciprocating the wash dispensing means towards, and away from, the surface of a conveyed slide element.

9. An analyzer as defined in claim 7, wherein the slide elements are dried elements that absorb wash liquid, and said spacing means further include a reference surface constructed to ride on said conveyed slide element surface, said reference surface being mounted relative to said dispensing means a predetermined height selected to provide a maximum rate of absorption of wash liquid in conveyed slide elements.

10. An analyzer as defined in claim 9, wherein said predetermined height is about 0.07 cm.

11. An analyzer as defined in claims 1 or 2, wherein said incubating means comprise a rotor and drive means for rotating said rotor constantly except when slide elements are being loaded and unloaded.

12. In a method of analyzing a body liquid for the concentration of an analyte present, such method comprising the steps of incubating at an incubation station, a slide element on which a body liquid has been dispensed, such slide element comprising the necessary reagents to produce a detectable signal in response to the presence of a particular analyte;

and thereafter detecting such detectable signal and converting it into a measure of concentration of the analyte;

the improvement wherein said method includes the steps of:

(a) before or during said incubating step, moving such slide element to a wash station located off-line and apart from said incubating station;

(b) after step (a), dispensing a wash liquid at said wash station onto the moved slide element; and thereafter (c) starting or finishing said incubating step at said incubation station.

* * * * *